(12) United States Patent
Fitzpatrick et al.

(10) Patent No.: US 8,641,690 B2
(45) Date of Patent: Feb. 4, 2014

(54) APPARATUS AND METHODS FOR TREATMENT OF HEMORRHAGING

(75) Inventors: Michael Connor Fitzpatrick, Abbotsford (CA); Robert Colin Adamson, North Vancouver (CA)

(73) Assignee: Micheal Connor Fitzpatrick, Abbotsford (CA)

( * ) Notice: Subject to any disclaimer, the term of this patent is extended or adjusted under 35 U.S.C. 154(b) by 649 days.

(21) Appl. No.: 12/682,572

(22) PCT Filed: Apr. 4, 2008

(86) PCT No.: PCT/CA2008/000657
§ 371 (c)(1), (2), (4) Date: Sep. 28, 2010

(87) PCT Pub. No.: WO2009/046518
PCT Pub. Date: Apr. 16, 2009

(65) Prior Publication Data
US 2011/0130739 A1    Jun. 2, 2011

Related U.S. Application Data

(60) Provisional application No. 60/979,020, filed on Oct. 10, 2007, provisional application No. 60/984,446, filed on Nov. 1, 2007.

(51) Int. Cl.
*A61F 13/00* (2006.01)
(52) U.S. Cl.
USPC .............. 604/304; 604/308; 606/203; 602/53
(58) Field of Classification Search
USPC ......... 604/304, 308; 602/53, 78, 79; 606/201, 606/203
See application file for complete search history.

(56) References Cited

U.S. PATENT DOCUMENTS 519,894 A * 5/1894 Shutz et al. ................... 602/60
3,171,410 A   3/1965 Towle, Jr. et al.
(Continued)

FOREIGN PATENT DOCUMENTS

EP    1295564    3/2003
GB      21060    0/1914
(Continued)

OTHER PUBLICATIONS

Excerpt from website www.zoomcomedic.com/en/0311.htm (accessed Mar. 28, 2008).

*Primary Examiner* — Lynne Anderson
(74) *Attorney, Agent, or Firm* — Oyen Wiggs Green & Mutala LLP

(57) ABSTRACT

An apparatus for treatment of external hemorrhaging has a panel for applying pressure to an absorbent pad and a wound on a body part. The panel has a central portion located between first and second arms which extend outwardly and in transversely opposed directions from the central portion. The apparatus includes a strap which is attached to the first arm at or near a first strap end, and is releasably attachable to the second arm at an attachment region of the strap spaced apart from the first strap end. When the panel is strapped to the body part, the tension in the strap pulls on and elastically deforms the first and second arms of the panel inwardly toward the body part, and applies localized pressure to the pad and wound.

20 Claims, 5 Drawing Sheets

(56) References Cited

U.S. PATENT DOCUMENTS

| | | |
|---|---|---|
| 3,954,109 A | 5/1976 | Patel |
| 4,377,159 A | 3/1983 | Hansen |
| 4,427,007 A | 1/1984 | Rexroth |
| 5,209,718 A | 5/1993 | McDaniel |
| 5,307,811 A | 5/1994 | Sigwart et al. |
| 5,507,721 A * | 4/1996 | Shippert ......................... 602/46 |
| 5,512,056 A | 4/1996 | Stevens et al. |
| 5,569,297 A | 10/1996 | Makower et al. |
| 5,628,723 A | 5/1997 | Grau |
| 5,643,315 A | 7/1997 | Daneshvar |
| 5,695,520 A | 12/1997 | Bruckner et al. |
| 5,968,072 A | 10/1999 | Hite et al. |
| 6,443,936 B1 | 9/2002 | Hamilton et al. |
| 6,593,508 B1 * | 7/2003 | Harder ............................ 602/56 |
| 6,827,727 B2 | 12/2004 | Stalemark et al. |
| 7,135,032 B2 | 11/2006 | Akerfeldt |
| 2003/0199922 A1 | 10/2003 | Buckman |
| 2008/0027365 A1 * | 1/2008 | Huey ............................. 602/44 |

FOREIGN PATENT DOCUMENTS

| | | |
|---|---|---|
| WO | 9908723 | 2/1999 |
| WO | 0043046 | 7/2000 |
| WO | 0174257 | 10/2001 |

* cited by examiner

APPARATUS AND METHODS FOR TREATMENT OF HEMORRHAGING

CROSS-REFERENCE TO RELATED APPLICATIONS

This application claims priority from U.S. provisional application No. 60/979,020 filed Oct. 10, 2007 entitled APPARATUS AND METHODS FOR TREATMENT OF HEMORRHAGING and U.S. provisional application No. 60/984,446 filed Nov. 1, 2007 entitled APPARATUS AND METHODS FOR TREATMENT OF HEMORRHAGING. For purposes of the United States of America, this application claims the benefit under 35 U.S.C. §119 of U.S. provisional application No. 60/979,020 filed Oct. 10, 2007 entitled APPARATUS AND METHODS FOR TREATMENT OF HEMORRHAGING and U.S. provisional application No. 60/984,446 filed Nov. 1, 2007 entitled APPARATUS AND METHODS FOR TREATMENT OF HEMORRHAGING both of which are hereby incorporated herein by reference.

TECHNICAL FIELD

This invention relates to treatment of hemorrhaging. Particular embodiments provide apparatus and methods for the treatment of external hemorrhaging on a body part.

BACKGROUND

First aid treatment of external hemorrhaging on a limb is typically administered by placing an absorbent pad on the wound and wrapping an elastomeric bandage (e.g. a Tensor® bandage) around the absorbent pad and limb. The bandage is typically wrapped around the limb one or more times and then affixed in place with a clasp. The bandage holds the absorbent pad on the wound and applies pressure to the wound.

Because the elastomeric bandage is wrapped around the limb, the bandage exerts generally uniform compression pressure around the circumference of the limb. This uniform pressure has a number of drawbacks. Since pressure is not localized at the wound site, but is distributed around the circumference of the limb, the pressure at the wound site may not be adequate to stop the blood flow. For severe bleeding, the bandage must be wrapped extremely tightly around the limb to apply sufficient pressure at the wound site to slow and stop the flow of blood. This extreme pressure can create serious discomfort for the patient and can also lead to a loss of circulation in the limb.

Devices for applying pressure to a wound are described in U.S. Pat. No. 5,512,056 (Stevens et al.), U.S. Pat. No. 7,135,032 (Åkerfeldt), U.S. Pat. No. 5,695,520 (Bruckner et al.), PCT Application Publication No. WO99/08723 (Magasi), Great Britain Patent No. 21, 060 (Carvell et al.) and U.S. Pat. No. 5,628,723 (Grau). However, the devices described in these references are difficult or time-consuming to apply, or cumbersome to wear. As such, these devices are not practical for use in emergency situations, combat situations, low light situations, self treatment situations or other situations in which there is only a limited time to treat a seriously wounded person. Such devices are limited in their applicability to circumstances where the injured person may need to resume activity while wearing the dressing on the wound.

There is a general desire for apparatus and methods for treatment of hemorrhaging which ameliorate at least some of these or other disadvantages with prior art hemorrhaging treatment devices.

SUMMARY

One aspect of the invention provides for apparatus for treatment of external hemorrhaging on a body part. In one embodiment, the apparatus includes a panel for applying localized pressure to a wound on a body part. The panel has a central portion located between first and second arms which extend outwardly and in transversely opposed directions from the central portion. The apparatus also has a strap extendable transversely from the first arm to the second arm and around a side of the body part opposing the wound. A length of the strap extending between the first and second arms determines a tension in the strap, the tension pulling inwardly on the first and second arms so as to cause the panel to apply pressure to the wound and to elastically deform the first and second arms inwardly toward the body part.

The apparatus may have a plurality of laterally spaced, transversely extending apertures defined in each of the first and second arms. Each of the apertures may have an outer transverse portion and an inner transverse portion, wherein the outer transverse portion has a greater area than the inner transverse portion.

In some embodiments, the strap is attached to the first arm and attachable to the second arm at one of a plurality of attachment regions along a portion of the strap. The panel may have one or more nibs extending from the second arm for insertion through one or more apertures at one of the attachment regions along the portion of the strap.

In some embodiments, a rigidity of the central portion is greater than a rigidity of the first and second arms. The central portion may have a thickness greater than a thickness of the first and second arms. The change in thickness of the panel between the central portion and each of the first and second arms may form a step. The step may zig-zag; laterally across the panel.

The central portion of the panel may be perforated by one or more holes. An inwardly facing surface of the panel may have a plurality of protrusions for gripping an absorbent pad placed over the wound and inwardly of the panel.

Another aspect of the invention provides for methods of treatment of external hemorrhaging on a body part. In one embodiment, the method comprises placing a panel over the wound, the panel having a central portion located between first and second arms which extend outwardly and in transversely opposed directions from the central portion; extending a strap transversely between the first and second arms and around a side of the body part opposite the wound; and adjusting a length of the strap extending between the first and second arms thereby creating tension in the strap pulling inwardly on the first and second arms to cause the panel to apply pressure to the wound and to elastically deform the first and second arms inwardly toward the body part. In some embodiments, the strap has a first strap end attached to the first arm, and the method comprises attaching the strap to the second arm at one of a plurality of regions along a portion of the strap, the attachment region determining the tension in the strap. In some embodiments, the step of attaching the strap to the second arm includes inserting one or more nibs extending from an end of the second arm through one or more apertures in the strap.

In some embodiments, the method of treatment of external hemorrhaging includes bonding an absorbent pad to an inwardly facing surface of the central portion of the panel prior to placing the panel with the pad over the wound. In other embodiments, the method includes placing a separate absorbent pad over the wound prior to placing the panel over the wound.

In addition to the exemplary aspects and embodiments described above, further aspects and embodiments will become apparent by reference to the drawings and by study of the following detailed descriptions.

BRIEF DESCRIPTION OF DRAWINGS

In drawings which illustrate non-limiting embodiments of the invention.

DESCRIPTION

Throughout the following description, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense. As used herein, "outward", "outwardly," "outwardmost" and similar words refer to directions which extend away from a center of a body part, but are not strictly limited to directions which extend radially away from the center. Conversely, "inward", "inwardly," "inwardmost" and similar words refer to directions which extend at least partially toward a center of a body part, but are not strictly limited to directions which extend radially toward the center.

Figure 1:
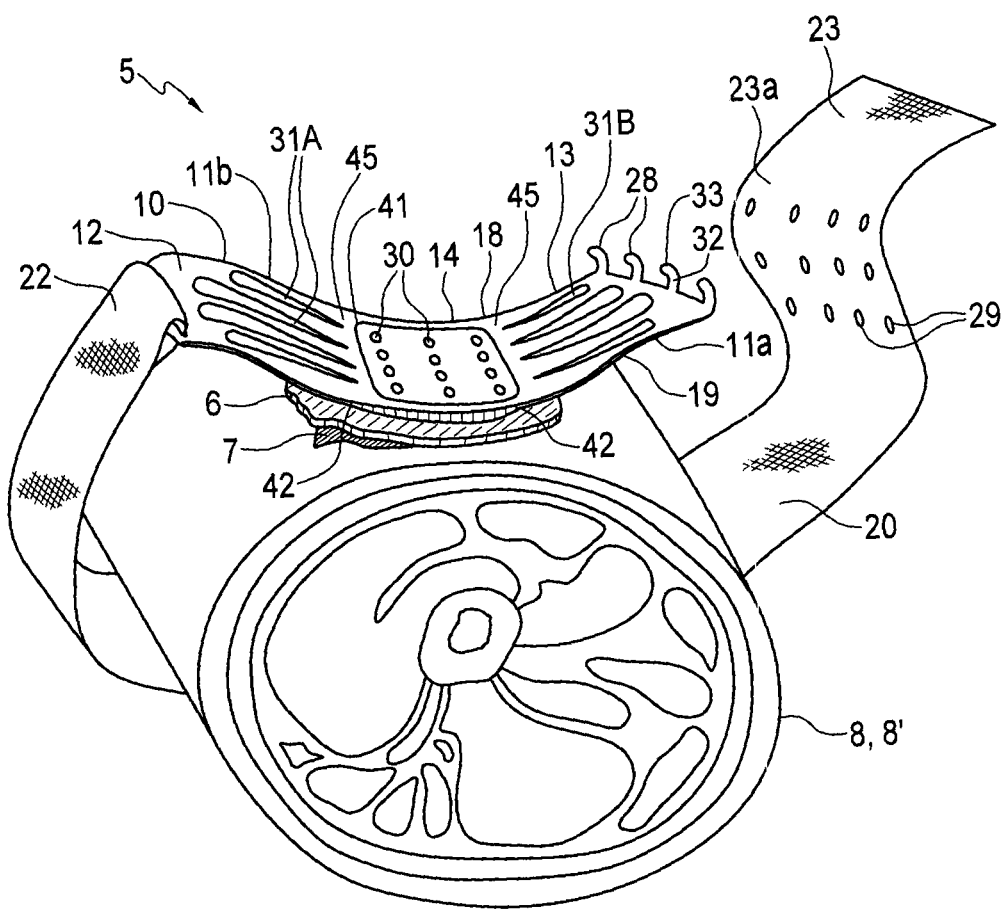
FIG. 1 is a side perspective view of a hemorrhage treatment apparatus according to a particular embodiment of the invention being applied to a portion of a limb (shown in cross-section)

FIG. 1 shows a hemorrhage treatment apparatus 5 for applying localized pressure against an absorbent pad 6 and a wound 7 on a body part 8. Body part 8 may be a limb (e.g. upper leg, lower leg, upper arm, lower arm or the like), or another part of the body such as the torso, abdomen, head or the like. In the exemplary illustrations included herewith, apparatus 5 is shown being applied on an upper portion of a longitudinally extending limb 8'. Accordingly, some of the directional language used to describe apparatus 5 relates to this orientation. It should be understood by those skilled in the art that apparatus 5 may be applied to other regions of limb 8' or to other body parts, in which case the orientations of apparatus 5 and the corresponding directions may be different. As such, directional language used in this description should be understood in an illustrative rather than a restrictive sense.

Apparatus 5 includes a curved panel 10. Panel 10 may be semi-rigid (e.g. sufficiently rigid to maintain its shape under its own weight and under the weight of the other components of apparatus 5) and elastically deformable (e.g. deformable under application of external force greater than that of its own weight). Panel 10 may generally be fabricated from any suitable material. The inventor has found that plastic materials provide panel 10 with desirable semi-rigid and elastically deformable characteristics.

As shown in FIG. 1, panel 10 has an inwardly facing surface 11a (which faces wound 7) and an outwardly facing surface 11b (which faces away from wound 7). Panel 10 incorporates a central portion 14 located between arms 12, 13 which extend outwardly and in transversely opposed directions from central portion 14. In the illustrated embodiment, central portion 14 and arms 12, 13 are integrally formed.

Panel 10 may have a transverse dimension spanning between a pair of opposed end edges 16, 17 and a width spanning between a pair of opposed side edges 18, 19. As shown best in FIG. 1, panel 10 may be oriented with its transverse dimension across limb 8', so that central portion 14 is positioned over pad 6 and wound 7, and arms 12, 13 extend from central portion 14 toward the transversely opposed sides of limb 8'. When the transverse width of limb 8' is less than the transverse dimension of panel 10, then arms 12, 13 may be positioned over the transversely opposed sides of limb 8'. However, when the transverse width of limb 8' is greater than the transverse dimension of panel 10, arms 12, 13 need not extend all the way to the opposed sides of limb 8'.

Figure 2:
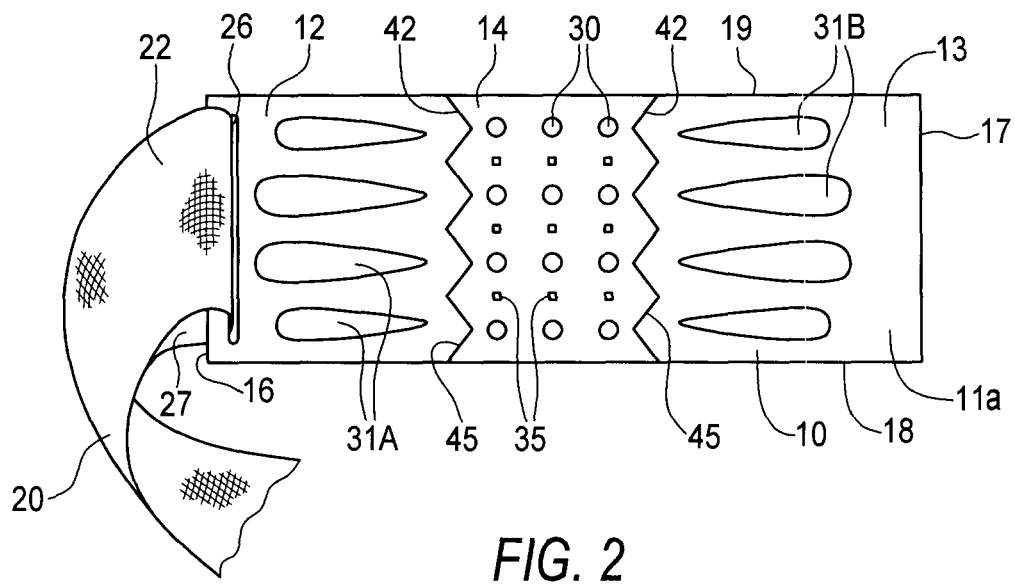
FIG. 2 is a bottom elevation view of the FIG. 1 hemorrhage treatment apparatus, showing the panel attached at one end to the strap.

Central portion 14 may be relatively more rigid than arms 12, 13, so that central portion 14 resists deformation as arms 12, 13 are pulled toward limb 8' by tension in strap 20. By way of non-limiting example, central portion 14 may be made more rigid than arms 12, 13 by augmenting the thickness of central portion 14 (in the inward-outward directions) relative to other portions of panel 10. In the illustrated embodiment of FIGS. 1 and 2, panel 10 has a generally constant thickness at central portion 14. At transition regions 45 between central portion 14 and arms 12, 13, the thickness of panel 10 (in the inward-outward directions) decreases by a step 42. As seen in FIG. 2, step 42 may zig-zag laterally across panel 10 between side edges 18, 19. The zig-zag shape of step 42 helps to distribute bending forces acting between central portion 14 and arms 12, 13 over a larger portion of panel 10, thereby reducing concentration of stress within panel 10.

In other embodiments, the thickness of central portion 14 may change by general discrete steps toward arms 12, 13, or taper gradually toward arms 12, 13, rather than decreasing by a step 42. For example, in the embodiment of panel 10 illustrated by FIG. 7 (which shares many of the same features as the embodiment of FIGS. 1 and 2), the thickness of panel 10 is greatest toward a center of central portion 14, and tapers gradually toward arms 12, 13.

In addition to, or instead of, altering thickness of central portion 14 relative to other portions of panel 10, the higher rigidity of central portion 14 relative to arms 12, 13 may be provided in other ways. For example, a plurality of apertures 31 may optionally be defined in arms 12, 13 to decrease the rigidity of arms 12, 13 relative to central portion 14. Apertures 31 make arms 12, 13 more flexible relative to central portion 14 and facilitate the deformation of arms 12, 13 as they are pulled toward limb 8' by strap 20 during operation of apparatus 5 (as will be described in further detail below). In the illustrated embodiments of FIGS. 1, 2 and 7, apertures 31 comprise a first plurality of laterally spaced apertures 31A extending transversely in arm 12 and a second plurality of laterally spaced apertures 31B extending transversely in arm 13.

Figure 3:
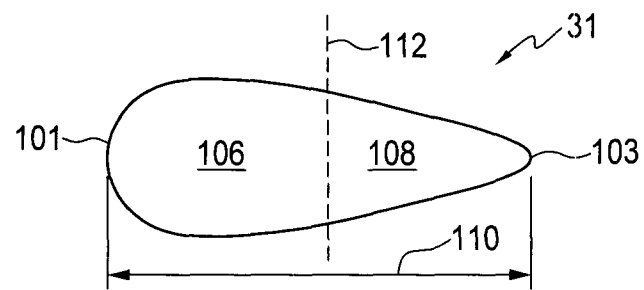
FIG. 3 is a top elevation view of an aperture defined in an arm of the FIG. 1 hemorrhage treatment apparatus.

As shown in FIG. 3, each of apertures 31 may have a transverse dimension 110 extending between an outer end 101 and an inner end 103 of aperture 31. A laterally extending midplane 112 bisects transverse dimension 110 to define an outer portion 106 of aperture 31 on a transverse outside of midplane 112 and an inner portion 108 of aperture 31 on a transverse inside of midplane 112. In preferred embodiments, outer portion 106 of aperture 31 has a greater area than inner portion 108 of aperture 31. The shape of apertures 31 provides greater flexibility to portions of arms 12, 13 surrounding outer portions 106 of apertures 31 relative to portions of arms 12, 13 surrounding inner portions 108 of apertures 31. In the illustrated embodiment, as seen in FIG. 3, apertures 31 have a generally teardrop shape. In other embodiments, apertures 31 may have a different shape, while still providing an outer portion 106 which has a greater area than inner portion 108.

Although not shown in the illustrated embodiment of FIGS. 1 and 2, reinforcing flanges (as will be described in further detail below with reference to FIG. 5) may extend transversely across panel 10 to increase the rigidity of central portion 14. In still other embodiments, central portion 14 may be fabricated from a different, more rigid material than arms 12, 13.

Figure 7:
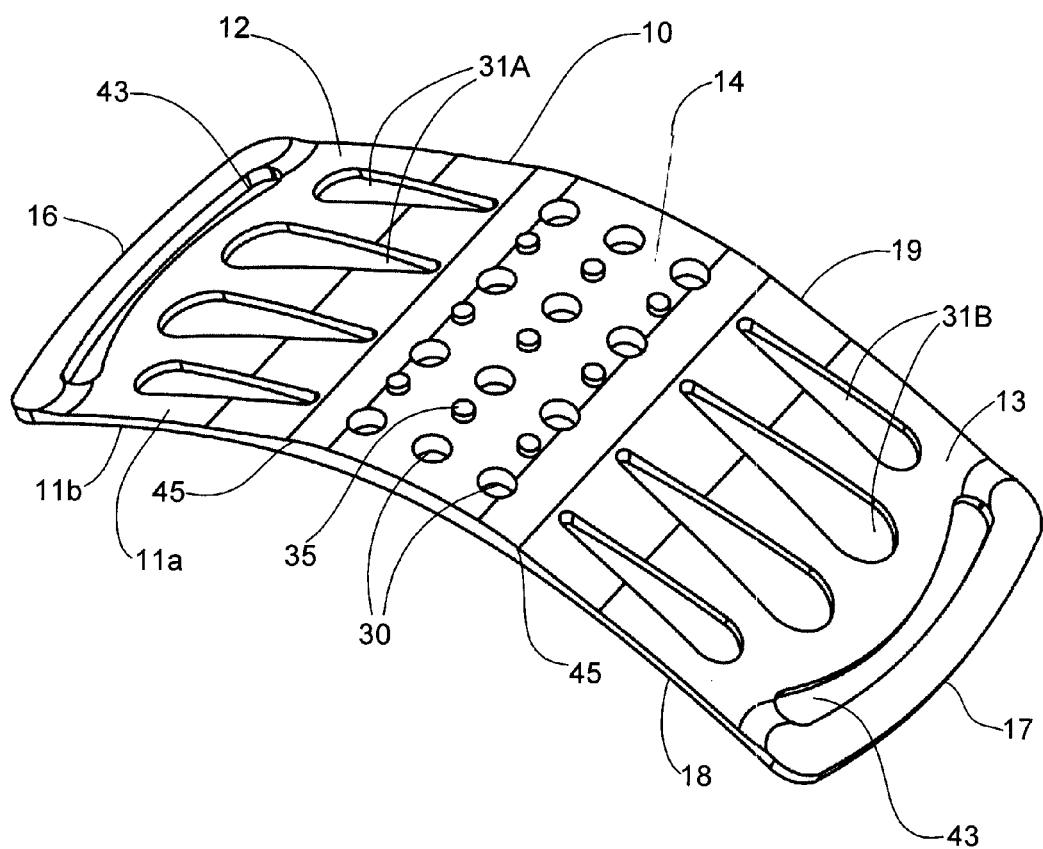
FIG. 7 is a perspective view of a panel of a hemorrhage treatment apparatus according to another embodiment of the invention, showing features on an undersurface of the panel.

Central portion 14 may be perforated by one or more holes 30 through which portions of pad 6 are visible. Holes 30 are large enough to permit inspection of pad 6 and determination of whether pad 6 is saturated, or whether pad 6 has shifted in location relative to wound 7 and requires repositioning. However, holes 30 are not too large so as to detract significantly from the rigidity of central portion 14. Holes 30 may have a total area which is smaller than a total area of apertures 31. Holes 30 may be arranged as rows of circular holes, as shown in FIGS. 1, 2 and 7, although any other suitable arrangement of holes 30 is also possible.

In some embodiments, central portion 14 optionally has a spoon-shaped concavity 41 on outwardly facing surface 11b. Concavity 41 may result in a more even distribution of pressure to wound 7.

Apparatus 5 also includes a strap 20 which extends between first and second strap ends 22, 23. Strap 20 may be made of elastomeric material, such as the material used for Tensor® bandages or the like. Strap 20 may have generally the same lateral width as panel 10, although this is not necessary. In some embodiments, strap 20 may have a width that is greater than or less than that of panel 10.

In the illustrated embodiment of FIG. 1, strap 20 is attached to arm 12 at or near first strap end 22. Strap 20 extends from first strap end 22 around limb 8' (on a side of limb 8' opposite panel 10) and is attachable to arm 13 at a strap connection portion 23a that is spaced apart from first strap end 22. Strap connection portion 23a may include second strap end 23. As explained in more detail below, in the illustrated embodiment of FIG. 1, strap connection portion 23a is releasably attachable to arm 13 at one of a plurality of regions along a length of strap connection portion 23a to adjust the tension in strap 20 and thereby adjust the force applied by panel 10 to wound 7.

As will be apparent to one of skill in the art, there are several ways of attaching strap 20 to arms 12, 13. For example, to attach strap 20 to arm 12 at or near first strap end 22, arm 12 may have a slot 26 adjacent to end edge 16 (FIG. 2). First strap end 22 may be pulled through slot 26 and may be sewed, glued or otherwise secured back to strap 20 to form a loop 27 which is coupled to arm 12 through slot 26.

To releasably attach strap connection portion 23a to arm 13, arm 13 may be provided with one or more nibs 28 for insertion through one or more corresponding apertures in strap connection portion 23a. In the illustrated embodiment of FIG. 1, arm 13 has a row of four nibs 28 projecting from arm 13 at laterally spaced locations along or near end edge 17.

Nibs 28 are insertable into a corresponding row of apertures 29 extending transversely across strap connection portion 23a. The lateral spacing of nibs 28 matches that of apertures 29. When nibs 28 are inserted through apertures 29, nibs 28 secure strap 20 to arm 13.

Each nib 28 may include a stalk 32 and a head 33 at the end of stalk 32, wherein head 33 has a cross-sectional dimension larger than that of stalk 32 to prevent nib 28 from slipping out of aperture 29. Also, stalk 32 may be oriented at a right angle or acute angle with respect to arm 13 to prevent nib 28 from slipping out of aperture 29, particularly when arm 13 is in an elastically deformed position as it is being pulled downwardly by strap 20. The deformation of panel 10 and arms 12, 13 is explained in more detail below. As shown in FIG. 1, parallel rows of apertures 29 may be provided at different regions along a length of strap connection portion 23a to allow strap 20 to be adjustably secured to arm 13 at any one of these regions. For a given strap 20 having a particular elasticity and other properties, the attachment region together with the circumference of limb 8' determine the tension in strap 20. For example, tightening of strap 20 may be accomplished by attaching strap 20 to arm 13 at an attachment region which is closer to first strap end 22. Conversely, loosening of strap 20 may be accomplished by attaching strap 20 to arm 13 at an attachment region which is farther away from first strap end 22.

In other embodiments, strap connection portion 23a may be releasably attached to arm 13 by any other suitable fasteners which permit adjustability of the tension in strap 20. For example, in the illustrated embodiment of FIG. 7, arms 12, 13 of panel 10 each have slots 43 adjacent to end edges 16, 17 respectively. First strap end 22 may be pulled through slot 43 on arm 12 and may be sewed, glued or otherwise secured back to strap 20 to form a loop which is coupled to arm 12 through slot 43. A length of strap connection portion 23a may be pulled through slot 43 on arm 13 and looped back to be removably attachable to itself by hook and loop fasteners (such as Velcro® fasteners), suitable clasps (such as the clawed clasps typically used with Tensor® bandages), clamps, or other suitable fastener(s). Slot 43 may also be combined with nibs similar to nibs 28 of the FIG. 1 embodiment, where strap connection portion 23a extends through the slot and then connects to the nibs. The length of strap connection portion 23a which is pulled through the slot together with the circumference of limb 8' determine the tension in strap 20.

Absorbent pad 6 may be provided as a separate component which is placed over wound 7. Panel 10 is subsequently placed over pad 6. Inwardly facing surface 11a of panel 10 may have a plurality of gripping teeth or other protrusions 35 (FIG. 2) for preventing pad 6 from sliding relative to panel 10. In other embodiments, inwardly facing surface 11a of panel 10 and/or an outwardly facing surface of pad 6 may be provided with other suitable attachment mechanisms, such as hook and loop fasteners or the like, which prevent movement of pad 6 relative to panel 10. In other embodiments, pad 6 may be bonded directly to inwardly facing surface 11a of panel 10 so that as panel 10 is placed over wound 7, pad 6 is simultaneously applied to wound 7. Prebonding pad 6 to panel 10 can save time in deploying apparatus 5, as it eliminates the separate step of placing pad 6 over wound 7 prior to placing panel 10 over limb 8'. Prebonding pad 6 to panel 10 also reduces the number of individual components that are packaged in a first aid kit to treat external hemorrhaging. Pad 6 may be removeably bonded to panel 10 (e.g. using adhesive tape or Velcro® fasteners) so that pad 6 can be replaced with a fresh absorbent pad when desired.

In currently preferred embodiments, panel 10 provides a central portion 14 for applying localized pressure to wound 7. Panel 10 and strap 20 may be sized appropriately for the specific limb 8' to which apparatus 5 is to be applied. For example, panel 10 and/or strap 20 may be larger for application to the upper leg, and smaller for application to the lower arm or the wrist. In addition, panel 10 may have variations in shape. For example, panel 10 may be provided with generally convex side edges 18, 19 so that a center part of central portion 14 is wider than the rest of panel 10.

In operation on a limb 8', panel 10 is placed transversely across a length of limb 8', so that central portion 14 abuts against pad 6 and wound 7, and arms 12, 13 extend outwardly from limb 8'. Strap 20 is extended around limb 8' (on the side opposite panel 10) and strap 20 is attached to arm 13 at a region of strap connection portion 23a. As explained above, strap connection portion 23a may be attached to arm 13 by inserting one or more nibs 28 on arm 13 through one or more apertures 29 in strap connection portion 23a. In other embodiments, strap connection portion 23a may be attached to arm 13 by pulling strap connection portion 23a through a slot in arm 13 and looping strap connection portion 23a to affix strap 20 to itself or to arm 13. The region of attachment between strap connection portion 23a and arm 13 is selected such that there is adequate tension in strap 20 to pull on arms 12, 13 causing panel 10 to apply pressure against pad 6 and wound 7. The tension in strap 20 may be adjusted by selecting a different attachment region within strap connection portion 23a (e.g. by inserting nibs 28 through a different row of apertures 29, or by pulling more or less of strap connection portion 23a through a slot in arm 13). In other embodiments, other mechanisms may be used to couple strap connection portion 23a to arm 13.

Figure 4A:
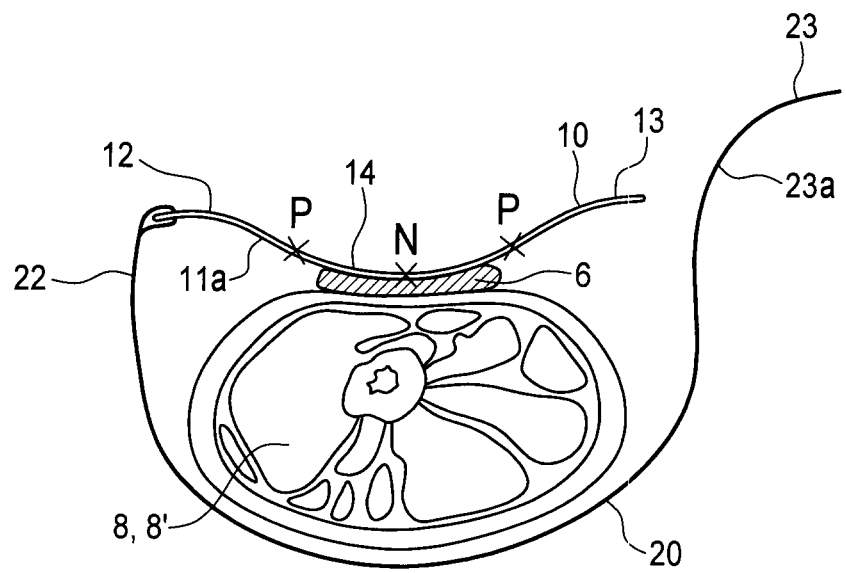
FIGS. 4A and 4B are side elevation views of a particular embodiment of a hemorrhage treatment apparatus, respectively depicting the panel in a relaxed state and under tension.
Figure 4B:
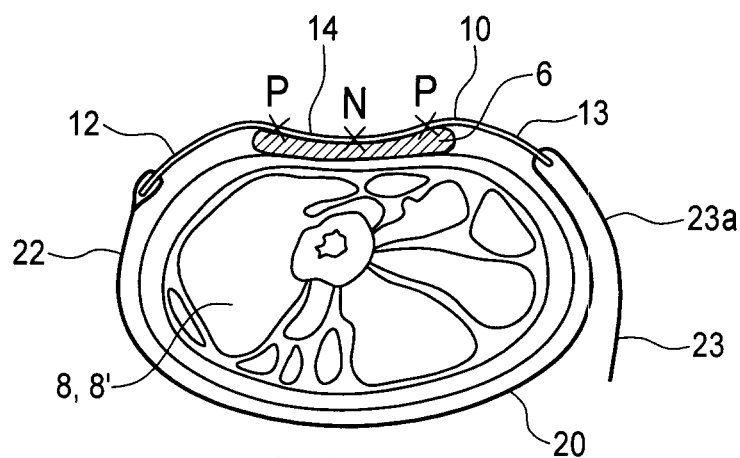

Upon application of tension to strap 20, arms 12, 13 may be elastically deformed from their relaxed shape (FIG. 4A) to a deformed shape (FIG. 4B). When panel 10 is not under tension, arms 12, 13 extend outwardly and in opposed transverse directions from central portion 14 (FIG. 4A). Arms 12, 13 are shaped such that, as seen in a side elevation view, there is an inflection point P (i.e. a point of conversion from convexity to concavity or vice versa) on each of arms 12, 13 which is spaced apart from a nadir N of central portion 14. As arms 12, 13 are pulled and deformed by strap 20, inflection points P shift toward nadir N as arms 12, 13 move inwardly toward limb 8' (as seen by comparing FIGS. 4A and 4B). When there is sufficient tension in strap 20 which pulls on arms 12, 13, panel 10 may be deformed such that arms 12, 13 are adjacent to, in contact with and/or wrapped around the sides of limb 8' (FIG. 4B). As described above, apertures 31 are optionally defined in arms 12, 13 to provide arms 12, 13 with a deformability greater than that of central portion 14, thereby facilitating the deformation of arms 12, 13 as they are pulled toward limb 8'. The elastically deformed shape of panel 10 shown in FIG. 4B is less obtrusive and permits the injured person to continue with his or her activities with minimal interference from panel 10.

To maintain pressure against pad 6 and wound 7, central portion 14 preferably deforms by a small amount relative to arms 12, 13 and may substantially maintain its original shape even as arms 12, 13 are deformed. As described above, the rigidity of central portion 14 is greater than that of arms 12, 13, so that central portion 14 resists deformation as arms 12, 13 are pulled by strap 20. If strap 20 is released from arm 13, panel 10 may resume its relaxed shape as seen in FIG. 4A.

When panel 10 is strapped to limb 8' in the manner described above, compression forces exerted by panel 10 against limb 8' are concentrated over wound 7 by central portion 14 of panel 10. The pressure applied at wound 7 may be greater than pressure applied at other locations around the circumference of limb 8'. Use of apparatus 5 may reduce the problem of restricted circulation caused by excessively high compression applied around the entire outer circumference of limb 8' (e.g. by a Tensor® bandage or the like).

As discussed above, holes 30 perforating central portion 14 permit visible inspection of pad 6. If pad 6 appears to be saturated, panel 10 may be temporarily removed, and one or more fresh pads for absorbing additional moisture may be placed onto the outward surface of saturated pad 6 before returning panel 10 to its position over wound 7 and strapping panel 10 to limb 8'. In other embodiments, one or more fresh pads may be placed onto outwardly facing surface 11b of panel 10 for absorbing additional moisture passing through holes 30 or around side edges 18, 19 of panel 10. The fresh pads may be secured in position by wrapping a strap around the pads and limb 8'. To increase pressure to wound 7, an additional apparatus 5 may be placed over the fresh pads and strapped to limb 8' in a similar fashion as for the already deployed apparatus 5.

Figure 5:
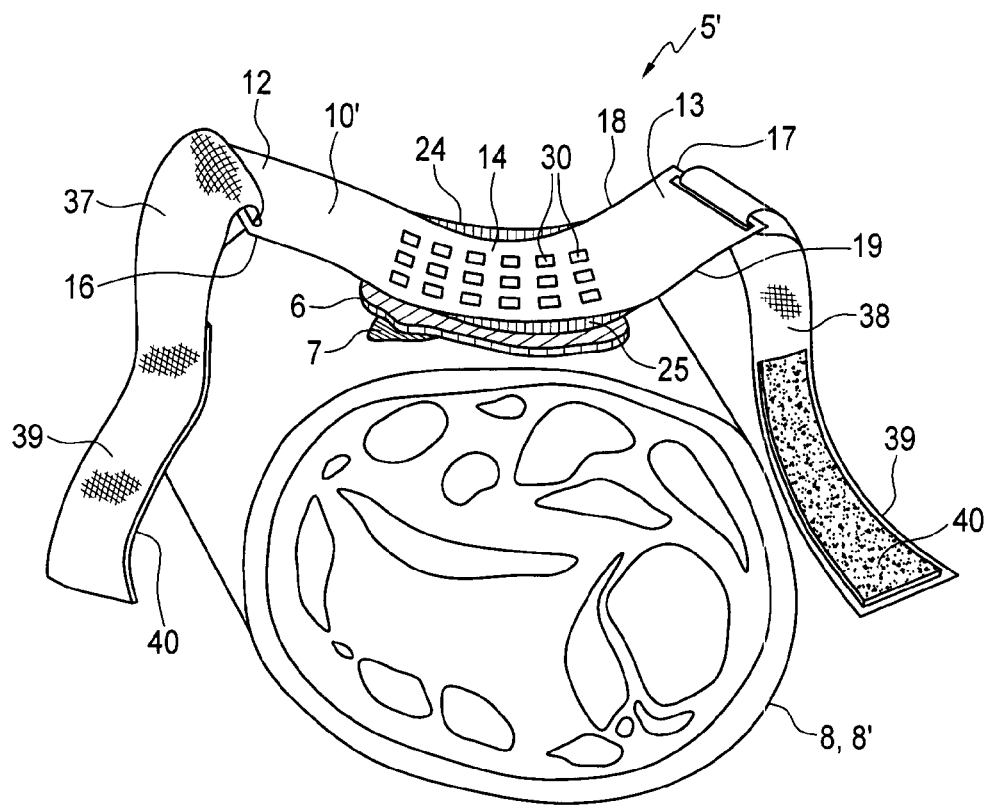
FIG. 5 is a side perspective view of a hemorrhage treatment apparatus according to another embodiment of the invention being applied to a portion of a limb (shown in cross-section)

FIG. 5 illustrates a hemorrhage treatment apparatus 5' according to another embodiment of the invention. Apparatus 5' may have particular application for body parts having a smaller circumference (e.g. wrist) or for smaller wounds. Apparatus 5' incorporates a panel 10' having similar features to panel 10 shown in FIGS. 1 and 2 and described above. However, rather than providing one strap which is affixed to arm 12 and releasably attachable to arm 13, apparatus 5' has a first strap 37 attachable to arm 12 and a second strap 38 attachable to arm 13. In the illustrated embodiment, straps 37, 38 are attached to panel 10' by pulling straps 37, 38 through respective slots in arms 12, 13 and looping each strap to affix the strap to itself.

Each of straps 37, 38 has adhesive 40 affixed to inwardly facing sides of the strap. In applying apparatus 5', contact portions 39 of straps 37, 38 are adhered (by way of adhesive 40) to locations on body part 8 such that there is tension in straps 37, 38 pulling on arms 12, 13 and causing panel 10' to exert pressure against wound 7. Tension in straps 37, 38 may also elastically deform arms 12, 13 as seen in FIG. 4B. Contact portions 39 may be adhered to opposed sides of limb 8' in a non-overlapping fashion, or in some embodiments, contact portions 39 may overlap with one another as they are adhered to limb 8' and/or to one another. To accommodate a range of limb sizes, and to provide a sufficient area of contact portions 39 for attachment to body part 8, adhesive 40 may extend along a region of each strap 37, 38, such as from a distal end of strap 37, 38 to a portion of strap 37, 38 which is proximate to arms 12, 13 of panel 10'.

In another embodiment, straps 37, 38 of apparatus 5' are not provided with adhesive 40, but are sufficiently long to extend around limb 8' and overlap with one another at a portion of limb 8'. For example, straps 37, 38 may overlap with one another on a side of limb 8' opposing wound 7. The overlapping ends of straps 37, 38 may be coupled together by a connector which may comprise a velcro fastener, ratcheting connector, or clasp, for example. The coupling of straps 37, 38 may be adjusted using the connector, to adjust the tension in straps 37, 38.

Panel 10' may have a pair of side flanges 24, 25 located adjacent side edges 18, 19, respectively, and projecting outwardly. Flanges 24, 25 extend across a transverse section of panel 10' to strengthen and reinforce panel 10'. Flanges 24, 25 may be larger and more pronounced toward the center of panel 10. In the illustrated embodiment of FIG. 5, flanges 24, 25 extend along a section of central portion 14, and taper as they extend transversely toward end edges 16, 17 so that arms 12, 13 do not have flanges. Flanges 24, 25 increase the rigidity of panel 10' at central portion 14. In some embodiments, panel 10' may have flanges spaced apart from side edges 18, 19. In still other embodiments, panel 10 (as illustrated in FIGS. 1 and 2) may incorporate flanges similar to flanges 24, 25 which may be spaced apart from side edges 18, 19.

Figure 6:
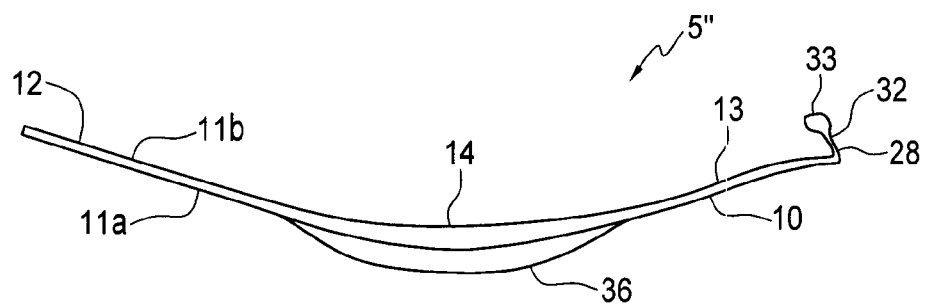
FIG. 6 is a side elevation view of a hemorrhage treatment apparatus according to yet another embodiment of the invention.

FIG. 6 illustrates a hemorrhage treatment apparatus 5″ according to another embodiment of the invention. Apparatus 5″ has similar features to those of apparatus 5. However, apparatus 5″ includes one or more transversely extending ribs 36 projecting from inwardly facing surface 11a at central portion 14 of panel 10. A rib 36 may be located proximate to each of side edges 18, 19 of panel 10. Rib 36 may be curved in shape, having an inward projection which increases toward a center of rib 36. When apparatus 5″ is applied to a limb 8' in the manner as described above with reference to FIGS. 4A and 4B, ribs 36 extend transversely across limb 8', applying localized pressure to limb 8' for constricting venous or arterial circulation. Ribs similar to ribs 36 may also be incorporated in other embodiments of the invention, such as in the illustrated embodiment of FIG. 5.

While a number of exemplary aspects and embodiments have been discussed above, those of skill in the art will recognize certain modifications, permutations, additions and sub-combinations thereof. For example:

While the particular embodiments of the hemorrhage treatment apparatus and methods described above are described in connection with application to a wound on a limb, it will be appreciated that the wound need not strictly be located on a limb, but may generally be located on any suitable body part. By way of non-limiting example, the hemorrhage treatment apparatus and methods described above may be applied to the torso, abdomen, head or any other suitable body part which requires direct pressure for the prevention, management or treatment of hemorrhaging.

The hemorrhage treatment apparatus and methods of the invention may be used to treat animals other than humans. For example, the apparatus and methods may be applied with suitable adaptations to treat hemorrhaging on the legs of horses.

The hemorrhage treatment apparatus and methods of the invention may be used to prevent, manage or treat hemorrhaging which may result from surgical procedures or operations in which body parts have been punctured by catheters or other objects. For example, for angiography of the femoral artery, a catheter is inserted into the femoral artery of a patient. Following the angiography, the patient is required to lie in a stationary position for some time while the post-operation wounds heal and to prevent re-opening of the surgical site on the leg. The apparatus and methods described herein may be applied to prevent, manage or treat hemorrhaging at the angiography puncture site on the patient's leg.

Apertures 31 may have shapes which are different than those that are shown in the illustrated embodiments. For example, apertures 31 may include an outer portion 106 which is generally shaped as a circle, oval or rectangle.

It is therefore intended that the following appended claims and claims hereafter introduced are interpreted to include all such modifications, permutations, additions and sub-combinations as are within their true spirit and scope.

What is claimed is:

1. An apparatus for treatment of hemorrhaging at a wound on a body part, the apparatus comprising:

a panel comprising inwardly and outwardly facing surfaces and a rigid or semi-rigid central portion located between first and second arms which extend outwardly and in transversely opposed directions from the central portion, wherein the first and second arms are relatively more flexible than the central portion; and a strap extendable transversely from the first arm to the second arm and around a side of the body part opposing the wound, wherein a length of the strap extending between the first and second arms determines a tension in the strap, the tension pulling inwardly on the first and second arms so as to elastically deform the first and second arms inwardly toward the body part;

wherein the first and second arms are sufficiently flexible so as to be deformed inwardly to be adjacent to the body part;

wherein a plurality of laterally spaced, transversely extending, rigidity-reducing apertures is defined in each of the first and second arms; and wherein each of the apertures has an outer transverse portion and an inner transverse portion, wherein the outer transverse portion has a greater area than the inner transverse portion.

2. An apparatus according to claim 1, wherein each of the apertures is tear drop shaped.

3. An apparatus according to claim 1, comprising one or more transversely extending ribs projecting from an inwardly facing surface of the panel.

4. An apparatus according to claim 3, wherein each of the one or more ribs have an inward projection which increases toward a center of the rib.

5. An apparatus according to claim 1, wherein the panel comprises one or more outwardly projecting, rigidity-enhancing flanges extending transversely across a section of the panel.

6. An apparatus according to claim 5, wherein the flanges have an outward projection increasing toward a center of the panel.

7. An apparatus according to claim 1, wherein the central portion has a thickness greater than a thickness of the first and second arms.

8. An apparatus according to claim 7, wherein a change in thickness of the panel between the central portion and each of the first and second arms forms a step.

9. An apparatus according to claim 8, wherein the step zig-zags laterally across the panel.

10. An apparatus according to claim 1, wherein the strap is attached to the first arm and attachable to the second arm at one of a plurality of attachment regions along a portion of the strap.

11. An apparatus according to claim 10, wherein the panel comprises one or more nibs extending from the second arm for insertion through one or more apertures at one of the attachment regions along the portion of the strap.

12. An apparatus according to claim 11, wherein each nib comprises a stalk and a head at the end of the stalk, wherein the head has a cross-sectional dimension larger than that of the stalk.

13. An apparatus according to claim 1, wherein the inwardly facing surface of the panel has a plurality of protrusions for gripping an absorbent pad placed over the wound and inwardly of the panel.

14. An apparatus according to claim 1, comprising an absorbent pad bonded to the inwardly facing surface of the panel.

15. An apparatus according to claim 1, wherein the central portion is shaped to curve inwardly toward the wound and retains its inward curved shape when the first and second arms are deformed inwardly.

16. An apparatus for treatment of hemorrhaging at a wound on a body part, the apparatus comprising:
- a panel comprising inwardly and outwardly facing surfaces and a rigid or semi-rigid central portion located between first and second arms which extend outwardly and in transversely opposed directions from the central portion, wherein the first and second arms are relatively more flexible than the central portion; and
- a strap extendable transversely from the first arm to the second arm and around a side of the body part opposing the wound, wherein a length of the strap extending between the first and second arms determines a tension in the strap, the tension pulling inwardly on the first and second arms so as to elastically deform the first and second arms inwardly toward the body part,
- wherein the central portion is perforated by one or more holes.

17. An apparatus for treatment of hemorrhaging at a wound on a body part, the apparatus comprising:
- a panel comprising inwardly and outwardly facing surfaces and a central rigid or semi-rigid portion located between first and second arms which extend outwardly and in transversely opposed directions from the central portion, wherein the first and second arms are relatively more flexible than the central portion;
- a first strap attachable to the first arm;
- a second strap attachable to the second arm; and
- adhesive applied to the first and second straps for adhering the straps to opposed sides of the body part at a respective contact region along a length of each strap;
- wherein the contact regions determine a tension of the straps, the tension pulling on the first and second arms so as to elastically deform the first and second arms inwardly toward the body part;
- wherein the first and second arms are sufficiently flexible so as to be deformed inwardly to be adjacent to the body part;
- wherein a plurality of laterally spaced, transversely extending, rigidity-reducing apertures is defined in each of the first and second arms;
- wherein each of the apertures has an outer transverse portion and an inner transverse portion, wherein the outer transverse portion has a greater area than the inner transverse portion.

18. An apparatus according to claim 17, wherein each of the apertures is tear drop shaped.

19. An apparatus according to claim 17, comprising an absorbent pad bonded to the inwardly facing surface of the panel.

20. An apparatus according to claim 17, wherein the central portion is shaped to curve inwardly toward the wound and retains its inward curved shape when the first and second arms are deformed inwardly.

* * * * *